United States Patent [19]

Blumenthal

[11] Patent Number: 4,643,214

[45] Date of Patent: Feb. 17, 1987

[54] PRESSURE MODIFYING SYSTEM

[76] Inventor: Michael B. Blumenthal, 807 Honeysuckle Crescent, Gallo Manor,, Ext'n 3, Sandton, South Africa

[21] Appl. No.: 700,447

[22] Filed: Feb. 11, 1985

[30] Foreign Application Priority Data

Feb. 15, 1984 [ZA] South Africa ............... 84/1089

[51] Int. Cl.⁴ ............................................. F17D 3/00
[52] U.S. Cl. ..................................... 137/12; 128/910
[58] Field of Search .................. 128/200.24, 204.18, 128/205.19, 205.24, 910; 137/12, 103, 907

[56] References Cited

U.S. PATENT DOCUMENTS 3,800,793  4/1974  Marrese et al. ............... 128/910 X
4,291,689  9/1981  Hay ................................. 128/910 X Primary Examiner—Stephen F. Husar
Attorney, Agent, or Firm—Robert H. Ware; Melvin I. Stoltz; Alfred A. Fressola

[57] ABSTRACT

A pressure modifying valve for anaesthetic gas scavenging systems for connection between a high vacuum source such as a hospital building service and the outlet from a patient or anaesthetic machine. The valve comprises a housing divided by a partition into two chambers having inlet and outlet ports respectively. The partition has a flow restricting orifice controlled by a valve member which is supported on a diaphragm to be self adjusting in response to pressure in the chamber. On the patient side, the pressure in chamber is controlled by pressure relief valves which are similar and interchangeable. The valve is made inexpensively of plastics and is disposable before the plastics deteriorates or undesirable matter accumulates and affects the functioning of the valve.

15 Claims, 4 Drawing Figures

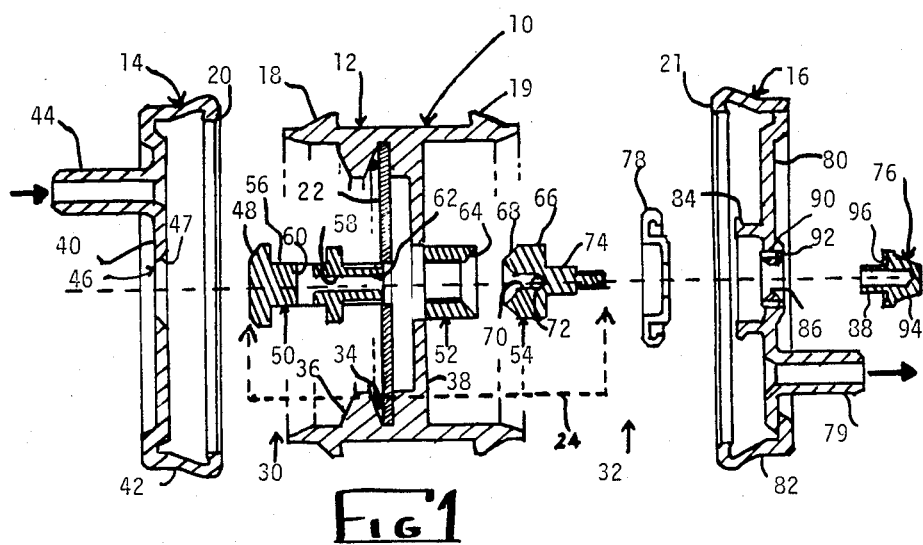
Fig 1
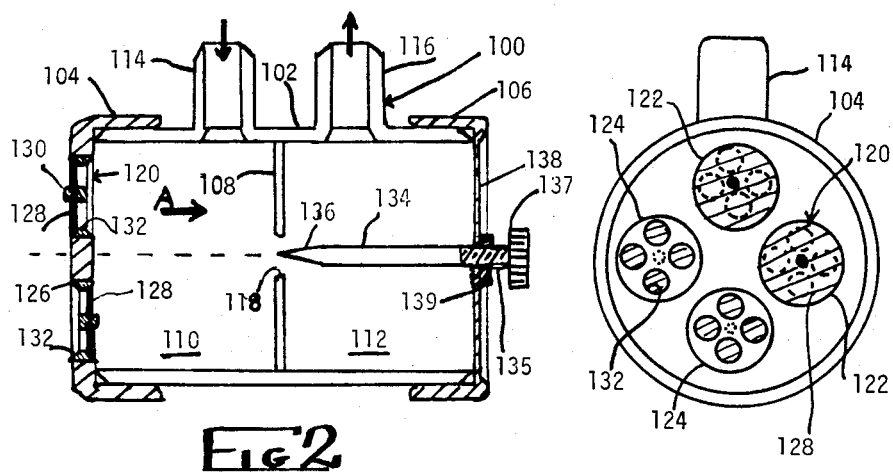
Fig 2
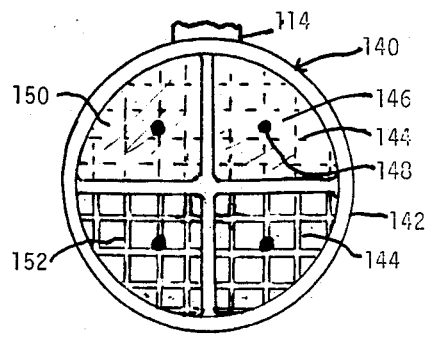
Fig 3
Fig 4

PRESSURE MODIFYING SYSTEM

FIELD OF THE INVENTION

This invention relates generally to a pressure modifying and regulating system. Primarily the invention is intended for use in an anaesthetic gas scavenging system, though the invention also has other applications in medicine, science and industry.

BACKGROUND TO THE INVENTION

Anaesthetic gas scavenging systems are used to eliminate or at least minimise the potential harmful effects, both immediate and long term, of anaesthetic gases on doctors and staff in the operating theatre. Apart from the usual air conditioning in a theatre, it is also known to provide a device for connecting the outlet from the patient or anaesthetic machine as well as any pressure relief or "pop-off" valves in the anaesthetic circuit to an exhaust means. The exhaust means may be a ventilation system or a vacuum system, the latter being either part of the "building services" or a specially provided service. See, for example, CSA Standard CAN 3-Z 168.8-M, Anaesthetic Gas Scavenging Systems, prepared and published by the Canadian Standards Association.

This invention is concerned with devices for use with vacuum systems. An example of such a device is disclosed in U.S. Pat. No. 4,291,689 W. W. Hay. The device comprises housing means forming a fluid path between an inlet port and an outlet port; a variable restriction means in the housing and forming a restriction of the fluid path; chamber means in the housing between the restriction means and one of the ports; and pressure relief valve means for venting the chamber means when a predetermined pressure limit is exceeded. Hereinafter a device of this type is referred to as "a device of the type set forth".

The restriction means of U.S. Pat. No. 4,291,689 is a needle valve settable by an operator, usually the anaesthetist, to establish a desired flow of gas to the vacuum system.

Experience by the inventor of several devices of this kind in an anaesthetic gas scavenging system has revealed several problem areas. A major problem is fluctuations of flow rate and pressure in the inlet chamber as the supply rate, ie from patient and anaesthetic gas supply, and vacuum pressure vary. With a building service vacuum supply the latter is practically unavoidable owing to the demands placed on the system by other users. Another major problem is the contamination of the device by the heavy components of the anaesthetic gases, such as Halothane and Penthrane. These components cause build up of tar which on the one hand blocks the needle valve and relief valves and on the other hand aggressively attacks the rubber and plastics elements and seals.

This invention seeks to overcome or at least ameliorate the above mentioned problems in a satisfactory, inexpensive manner.

SUMMARY OF THE INVENTION

According to one aspect of the invention there is provided a method of modifying pressure in a fluid path including the steps of forming a variable restriction in the fluid path control the flow of fluid to the path and venting the fluid path on one side of the restriction when a predetermined pressure limit is exceeded on that side of the restriction, with the improvement of including the further steps of:
sensing the fluid pressure on at least one side of the restriction;
generating a movement in response to the sensed pressure; and
applying the movement to vary the restriction to control the flow of fluid in the path automatically in response to changes in the sensed pressure.

The restriction may be varied to maintain at least one of the pressure on one side of the restriction and the volumetric flow rate therethrough substantially constant as the pressure differential across the restriction varies.

According to another aspect of the invention a device of the type set forth has the improvement of including actuating means sensitive to and movable in response to pressure in the housing on at least one side of the restriction means, the actuating means being connected to a part of the restriction means to control the restriction means in response to the sensed pressure.

Preferably the actuating means is a diaphragm. The diaphragm may be an external wall portion of the housing with one side of the diaphragm being exposed to the pressure to be sensed and the other side being exposed to the exterior of the housing. Alternatively, the diaphragm may be an internal wall portion in the housing forming a wall portion of the chamber means in parallel with the restriction means to sense the pressure differential across the restriction means. In this embodiment the diaphragm may support or be formed with an orifice defining component of the restriction means.

The diaphragm may also actuate at least one vent through the housing to provide communictation between the fluid path and the exterior of the housing.

The restriction means is preferably a needle valve with an orifice component and a needle component one of which is connected to the acutating means.

Preferably there are positive and negative pressure relief valve means. Preferably there are a plurality of positive and negative pressure relief valve means which are similar and interchangeable and thereby installable in suitable combinations to provide at least approximations of desired capacities for the positive and negative pressure relief.

Preferably the device is made of suitable plastics materials. With this development the device may be easily installed in any operating theatre since it automatically accommodates itself to prevailing conditions while it will be of relatively low cost and therefore be disposable, such as on a daily basis, before the plastics deteriorates or undesirable tar build-up occurs.

Further features, variants and objects of the invention will become apparent from the following description made with reference to the accompanying schematic drawings of embodiments of the invention suitable for an anaesthetic gas scavenging system using a vacuum exhaust system.

BRIEF DESCRIPTION OF THE DRAWINGS

FIG. 1 shows an exploded view, partly in section, of an embodiment of the device of the invention;

FIG. 2 shows partly in section another embodiment of the device of the invention;

FIG. 3 shows an end view along the direction of arrow A in FIG. 2, illustrating the arrangement of the pressure relief valves of the device of FIG. 2; and FIG. 4 shows a view similar to that of FIG. 3 illustrating an alternate form of construction of the pressure relief valves.

DESCRIPTION OF PREFERRED EMBODIMENTS

Referring to FIG. 1 of the drawings, there is shown a pressure modifying and regulating device including a housing 10 comprising a cylindrical body part 12 and end caps 14 and 16 which are clipped on to the body part 12 by means of interengaging peripheral rib 18 and 19 and lip 20 and 21 formations. A resilient diaphragm 22 is supported in the body 12. The diaphragm 22 together with a restriction means 24 divides the housing 10 into an inlet chamber 30 and an outlet chamber 32. The diaphragm is sealably clamped to the body 12 by a wire circlip 34 with the peripheral region of the diaphragm and the circlip 34 being received in an annular groove formed between a radially inward extending rib 36 and a radially inward extending wall 38. The wall 38 has a portion extending further radially inwards to the restriction means 24 and provides a guide therefor.

The end cap 14 has a body portion 40 and a flange portion 42 on which the lip 20 is formed. The body portion 40 has a spigot 44 which defines an inlet port for the housing 10. The body portion 40 also has an opening 46 with a bevelled edge forming a valve seat 47 facing the interior of the housing. A valve member 48 on the end of the valve means 24 is arranged to seal against the seat 47.

The restriction means 24 is in three parts, namely a body part 50, and sleeve part 52 and a valve member 54. The parts 50 and 52 threadably engage each other and clamp on to the diaphragm 22. The body part 50 comprises a shank portion 56 having an axial bore 58 which intersects a cross-bore 60 at one end and which terminates at the other end in a conical depression 62 which blends flush with a conical indentation 64 on the sleeve 52 when the sleeve 52 and body part 50 are firmly engaged with each other and the diaphragm 22.

The valve member 54 has a body portion 66 formed with a convex end face 68, complementary to the bevelled faces 62 and 64 so that when the parts are engaged a seal is formed therebetween. The body portion 66 also has an axial bore 70 which opens into communication with the bore 58 of the part 50 at one end and intersects lateral bores 72 at its other end. The bores 72 have a combined cross-section which is less than the cross-section of the bore 58. The valve member 54 has a tail portion 74 that is partially threaded to engage a relief valve member 76 to lock the two parts 54 and 76 to move together.

A cap member 78 is provided to serve as an axial guide and rotational locking member for the valve member 54 when it is being screwed into engagement with the member 76. For the locating function the shank 74 of the member 54 is oval and the corresponding hole in the cap member 78 is similarly oval.

The end cap 16 includes a body portion 80 having a spigot 79 forming and outlet port and having a flange 82 on which the lip 21 is formed. The body portion 80 has an internal anular rib 84 on to which the cap member 78 can clip. The central portion of the body 80 is formed with a hole 86 in which a shank portion 88 of the part 76 can slidably move. Radially spaced from the hole 86 are holes 90 which comunicate with an annular groove 92. The valve member 76 includes a head 94 one side of which is formed to seal against the body 80 by means of an annular ridge 96 that aligns with groove 90. The head 94 is knurled.

In practice the device operates as follows: High pressure may be applied to the port 44 or low pressure may be applied to the port 79 so that fluid will flow in the direction of the arrows shown. This fluid will enter the chamber 30 pass through the bores 60 and 58 into the chamber 32 from which it will be exhausted via the port 79. Should there be an excessively low pressure in the chamber 32 or an excessively high pressure in the chamber 30, depending on whether the device is connected to a vacuum supply or a pressure supply, then the diaphragm 22 and parts 50 and 52 will move towards the right in the drawing. After an initial movement, the bevelled surfaces 62, 64 and 68 will mate so that the fluid will pass from the bore 58 in to the bore 70 and then through the cross bores 72. Since the cross bores 72 are of a combined cross-sectional area which is smaller than that of the bore 58 a further restriction will be applied to the fluid flow between the chambers 30 and 32. This rate of change of fluid flow will be gradual as the parts 50, 52 and 54 mate with each other progressively.

As the parts 50 and 52 move to the right with the diaphragm 22, the valve member 48 also moves away from the seat 47 so allowing pressure relief for the chamber 30. Thus the pressure in chamber 30 will remain negative, but only to a small degree below atmospheric.

If a low pressure in excess of that which can be controlled by the further restriction of the flow path is present in chamber 32, then the diaphragm will move further to the right and cause the valve 76 to open. This will allow communication of the low pressure chamber 32 with atmosphere to provide pressure relief for that chamber and ultimately to regulate the pressure in chamber 30.

For use of the device of FIG. 1 in an anaesthetic gas scavenging system the port 79 will be connected to a hospital or theatre vacuum exhaust system while the port 44 will be connected to a patient or anaesthetic machine to extract anaesthetic gases which would otherwise simply escape into the theatre. In practice the hospital suction is a fluctuating high vacuum, e.g. 40 to 80 kPa, while the maximum pressure which can be applied to a patient is minus 5 mm of $H_2O$, or $-50$ Pa, (and much less for children) so as to avoid collapsing the patient's lungs. A further requirement is that the flow rate should be at least 15 L/min and preferably 25 to 30 L/min.

This required pressure differential is very large, while the pressure which is most likely to vary is that of the hospital suction. Accordingly, the device is set to provide a desired minimum pressure for the patient while maintaining a reasonable extraction rate of gases. The initial setting is obtained by correct dimensioning of the bore 58, bores 72 and the stiffness of the diaphragm. Finer setting of the device is obtained by adjusting the amount by which the members 54 and 76 are screwed into each other to predetermine the amount by which the diaphragm 22 and parts 50 and 52 have to move to seat against the valve member 54 in order to restrict the passage between chambers 30 and 32 so as to vary the pressure in the low pressure chamber 32. Should the vacuum pressure increase, ie become more negative, in use, then the vent on the right hand side will open and allow the vacuum pressure to decrease so that the patient will not be affected. Should the suction pressure decrease, ie become less negative, then at worst the amount of gases which will be extracted from the patient will decrease and anaesthetic gases may escape into the theatre, but no excessive negative pressures or otherwise will be applied to the patient: this condition is accepted as unavoidable in order to maintain patient safety. The vent formed in the chamber 30 also ensures that should the suction pressure increase to too great an extent, ie become more negative, then air will simply be drawn through the vent into the chamber 30. Again the patient will not be harmed, though an additional load will be placed on the vacuum system.

As a modification of the device described above one or both of the conical surfaces 47 and 48 may be provided with axially extending ribs or pimples so that the vent never closes properly and a continuous bleed of atmospheric air into the chamber 30 will take place.

As a further modification either of the vents for the chambers 30 or 32 may be omitted, but this is not desirable for safety reasons. Should the device be used for applications other than medical use then such removal may be acceptable.

A metal coil spring or plastic spring may be provided between lid 80 or cap 78 and member 54 to bias valve members 54 and 76 to a rest position.

Tests have shown that a convenient size for the bore 58 is approximately 6 mm though it may vary between 3 and 10 mm depending on the particular application and vacuum system. A preferred range being between 2 and 7 mm. The cross-bores 72 in the valve member 54 are conveniently between 1.5 and 8 mm in diameter, the size being determined in relation to the diameter of the bore 58, the stiffness of the diaphragm 22 and the effectiveness of the seal between the conical faces 68 with 62 and 64, so as to reduce the area by 20 to 40%.

FIG. 2 shows a variant 100 of the device of the invention which is believed to be simple and inexpensive to manufacture in suitable plastics materials. The device 100 comprises a round cylindrical housing 102, end caps 106 and 104 closing off opposite ends of the housing, and an internal partition wall 108 dividing the housing into an inlet chamber 110 and an outlet chamber 112. A spigot 114 forms an inlet port to the inlet chamber 110 and a spigot 116 forms an outlet port from the chamber 112.

The partition wall 108 is relatively stiff, ie substantially inflexible when exposed to the expected pressures prevailing in a hospital vacuum system. The partition 108 is formed with a central axial orifice 118 having bevelled or radiused edges at both ends. These edges promote smooth flow through the orifice to reduce noise from the device, such as whistling and hissing, and to ensure stable performance of the device over extended periods.

With reference to FIGS. 2 and 3 it can be seen that the end cap 104 is provided with four pressure relief valves 120 which are substantially identical and which are arranged such that there are two positive pressure relief valves 122 and two negative pressure relief valves 124. Each valve 120 comprises a circular body portion 126 dimensioned to be a snug, press fit in a corresponding hole in the end cap 104 and a flexible, circular, thin sheet of plastics 128 seated on the body portion 126 and held thereon by a headed stud 130. The body portion is formed with a plurality of through holes 132. The valves 120 are interchangeable and may be set or arranged to achieve any desired combination of volumes for the negative and positive pressure relief. The end cap 106 carries a centrally mounted pin 134 the head or distal portion of which 136 is tapered and dimensioned to fit into the orifice 118 and restrict its cross-sectional area. The body portion of 138 of the end cap 106 is made of a relatively thinner plastics material so that it can deflect resiliently under the influence of the pressure differential between atmosphere outside the device and the negative pressure prevailing in the chamber 112.

The cross-sections of the orifice 118 and needle 136 are tailored in relation to the flexibility of the body portion or diaphragm 138 such that, within an expected pressure range, movement of the needle 136 into the orifice 118 will control the pressure in the chamber 110 as well as the flow rate through orifice 118 to be substantially constant. It has been found that the diameter of the orifice 118 should be between 3 and 8 mm, while the needle 136 on maximum insertion into the orifice 118 should decrease its cross-sectional area by 20 to 50% of its free cross-sectional area, e.g. decrease by 30% for a pressure change of 40 to 80 kPa. It has also been found that the length of the needle 136 should be between 2 and 8 mm, preferably 4 mm and be used with an appropriate stiffness body portion 138 to allow for full movement of the needle into the orifice 118. Any excessive high or low pressures in chamber 110 caused either by changes in vacuum pressure or in supply rate to the chamber from the patient side will be accommodated by the pressure relief valves 120, compressibility of the gases at these pressures and the "re-breather bag" normally used. For this purpose the pressures at which the relief valves 120 will open will be determined by the stiffness of the sheet 128.

The pin 134 also has, at the end remote from the needle 136, a threaded portion 135 terminating in a ribbed head 137, with the portion 135 engaged in a threaded bore in a boss 139 on the body 138. This construction allows the needle to be pre-set with respect to the orifice 118 to accomodate manufacturing tolerances or variations in vacuum pressure beyond those normally expected.

The device 100 is designed to be manufactured in suitable plastics materials so that it will be of relatively low cost and be disposable. The range of plastics which may be used is wide and the choice within the knowledge of a person skilled in the art. The device has a body 102 of clear or at least translucent plastics so that the build up of tars therein can be observed and the device replaced before it becomes blocked or the plastics deteriorate. As alternatives, certain of the plastics components may be pigmented to change colour after a predetermined exposure to the heavy gases or may have a colour changing reagent coating applied internally over selected regions.

In practice, the device 100 is installed between an appropriate position in the breathing or anaesthetic circuit and the vacuum system, the particular arrangement being dependent on the anaesthetic circuit.

If necessary the device is pre-set by rotating the head 137 to adjust the needle 136 such that the normally installed "re-breather" bag is appropriately distended, ie approximately 10% to 20%, without collapsing or being overinflated. Thereafter the device will be self-adjusting to prevailing conditions.

FIG. 4 shows a variant 140 of end cap for the chamber 110 of FIG. 2. In principle this end cap is similar to that of FIG. 3 except that the body portion 142 is divided into four quadrants 144 each of which has an open mesh configuration. A thin plastics sheet 146 is secured over each quadrant at a position near the centre of each guadrant 146 by means of a headed stud 148. Again the sheet may be secured either inside or outside the end cap to provide either a positive 150 or negative 152 pressure relief valve.

It is to be understood that the invention is not limited to the precise constructional details shown in the drawings and described above and many modifications may be made to these embodiments without departing from the spirit of the invention or the scope of the claims. For example the cylindrical body portion of the device may be round or polygonal in cross-section. With the embodiment of FIGS. 2 and 3, instead of having the partition 108 being relatively stiff it may also be made flexible so that it will move with repsect to the needle 136 in response to the pressure differential between the chambers 110 and 112.

Furthermore the needle and orifice arrangement of FIG. 2 may be used in the embodiment of FIG. 1, ie by replacing the valve member 54 with a suitable shank having a needle movable into the bore 58. It is also possible with the embodiment of FIG. 2 to use a double needle arrangement, ie in addition to the needle 136 on a flexible end cap portion 138 to have in addition a further needle, not shown, supported on the end cap 104 with the end cap being flexible. Also suitable pressure relief valves may be provided in the end cap 106. Also the needle 136 need not be conical as shown, but could have a convex or concave cross-section.

What is claimed is:

1. A method of modifying pressure in a fluid path including the steps of forming a restriction in the fluid path to control the flow of fluid in the path and venting the fluid path on one side of the restriction when a pre-determined pressure limit is exceeded, with the improvement of including the further steps of:
    sensing the fluid pressure on at least one side of the restriction; generating a movement in response to the sensed pressure; and
    applying the movement to varying the restriction to control the flow of fluid in the path.

2. A method as claimed in claim 1, in which the restriction is varied to maintain at least one of the pressure on one side of the restriction and the flow rate through the restriction substantially constant as the pressure differential across the restriction varies.

3. A pressure modifying device comprising:
    housing means forming a fluid path between an inlet port and an outlet port;
    a restriction means in the housing and forming a restriction of the fluid path;
    a chamber formed in the housing between the restriction means and one of the ports; and
    pressure relief valve means for venting the chamber when a predetermined pressure limit in the chamber is exceeded;
with the improvement of
    actuating means sensitive to and movable in response to pressure in the housing on at least one side of the restriction means;
    the actuating means being connected to a part of the restriction means to control the restriction means in response to the sensed pressure.

4. A device as claimed in claim 3, in which the actuating means is a diaphragm.

5. A device as claimed in claim 4, in which the diaphragm constitutes an external wall portion of the housing with one side of the diaphragm being exposed to the pressure to be sensed and the other side being exposed to the exterior of the housing.

6. A device as claimed in claim 4, in which the diaphragm is an internal wall portion in the housing forming one wall portion of the chamber means in parallel with the restriction means to sense the pressure differential across the restriction means.

7. A device as claimed in claim 3, in which the actuating means also actuates at least one vent through the housing to provide communication between the fluid path and the exterior of the housing.

8. A device as claimed in claim 3, which is made of suitable plastics materials, the device being adapted to indicate accumulation of undesirable matter.

9. A device as claimed in claim 3, in which the pressure relief valve means includes a plurality of positive and negative relief valves which are similar and interchangeable.

10. A pressure modifying device comprising:
    a housing including a cylindrical body portion with an end cap closing each end of the body portion;
    partition means in the housing dividing its interior into first and second chambers;
    an inlet port communicating with the first chamber;
    an outlet port communicating with the second chamber;
    a flow restricting orifice formed through the partition means whereby a fluid path is formed comprising the inlet port, the first chamber, the orifice, the second chamber and the outlet port;
    valve means to vary the cross-section of the orifice; and
    pressure relief valve means for venting at least one of the chambers when a predetermined pressure limit in the chamber is exceeded.

11. A device as claimed in claim 10, in which at least one of the partition means and valve means is movable relatively to the housing automatically in response to variations in pressure in the second chamber.

12. A device as claimed in claim 11, in which the partition means is resiliently flexible and constitutes said relatively movable means, the partition means being movable in response to the pressure differential between the first and second chambers to adjust the position of the orifice with respect to the valve means.

13. A device as claimed in claim 11, in which one end cap is resiliently flexible and the valve member is supported on said flexible end cap to constitute said relatively movable means.

14. A device as claimed in claim 11, in which said relatively movable means is responsive to the pressure in the second chamber and the pressure relief valve means is responsive to the pressure in the first chamber.

15. A device as claimed in claim 10, which is made of suitable plastics materials and which is adapted to reveal the presence of accumulation of undesirable matter in the device.

* * * * *